(12) United States Patent
Li

(10) Patent No.: US 8,067,069 B2
(45) Date of Patent: Nov. 29, 2011

(54) STRONTIUM-SUBSTITUTED APATITE COATING

(75) Inventor: Panjian Li, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1221 days.

(21) Appl. No.: 11/121,407

(22) Filed: May 4, 2005

(65) Prior Publication Data
US 2005/0208097 A1   Sep. 22, 2005

Related U.S. Application Data

(62) Division of application No. 10/448,685, filed on May 30, 2003, now Pat. No. 6,905,723.

(51) Int. Cl.
| | |
|---|---|
| A61B 17/58 | (2006.01) |
| A61F 2/02 | (2006.01) |
| A61F 2/28 | (2006.01) |
| A61F 2/30 | (2006.01) |
| A61F 13/00 | (2006.01) |
| A61K 33/42 | (2006.01) |
| B32B 1/00 | (2006.01) |

(52) U.S. Cl. ............. 428/34.4; 428/35.7; 428/36.5; 424/422; 424/602; 606/76; 623/11.11; 623/23.56; 623/23.57

(58) Field of Classification Search ........... 428/34.1, 428/34.4, 35.7, 35.8, 36.6, 36.7, 36.8, 36.9, 428/36.92, 36.5; 606/76, 77; 623/11.11–23.46; 424/422–426, 406, 602, 604
See application file for complete search history.

(56) References Cited

U.S. PATENT DOCUMENTS

| | | | |
|---|---|---|---|
| 4,596,574 A | 6/1986 | Urist | |
| 5,068,122 A | 11/1991 | Kokubo et al. | |
| 5,128,367 A | 7/1992 | Wierzbicki et al. | |
| 5,188,670 A | 2/1993 | Constantz | |
| 5,205,921 A | 4/1993 | Shirkanzadeh | |
| 5,258,029 A | 11/1993 | Chu et al. | |
| 5,441,536 A | 8/1995 | Aoki et al. | |
| 5,700,289 A | 12/1997 | Breitbart et al. | |
| 5,824,651 A | 10/1998 | Nanci et al. | |
| 6,129,928 A | 10/2000 | Sarangapani et al. | |
| 6,136,369 A * | 10/2000 | Leitao et al. ............... | 427/2.27 |
| 6,139,585 A | 10/2000 | Li | |
| 6,180,606 B1 | 1/2001 | Chen et al. | |
| 6,183,711 B1 | 2/2001 | Nakamoto et al. | |
| 6,207,218 B1 | 3/2001 | Layrolle et al. | |
| 6,280,789 B1 | 8/2001 | Rey et al. | |
| 6,312,468 B1 | 11/2001 | Best et al. | |
| 6,338,810 B1 * | 1/2002 | Carpena et al. ............ | 264/16 |
| 6,461,385 B1 | 10/2002 | Gayer et al. | |
| 6,733,503 B2 * | 5/2004 | Layrolle et al. ............ | 606/77 |
| 7,087,068 B1 | 8/2006 | Marshall et al. | |
| 2001/0038848 A1 | 8/2001 | Donda et al. | |
| 2001/0053406 A1 | 12/2001 | Layrolle et al. | |
| 2002/0127711 A1 | 9/2002 | Kale et al. | |

FOREIGN PATENT DOCUMENTS

| | | |
|---|---|---|
| EP | 0 511 868 A2 | 11/1992 |
| EP | 0 548 365 A1 | 6/1993 |
| JP | 4024883 B2 | 12/2007 |
| WO | 9741273 | 11/1997 |
| WO | WO 01/49327 A2 | 7/2001 |
| WO | 0183367 | 11/2001 |

OTHER PUBLICATIONS

Wikipedia.com entry of "Carbonate", accessed Oct. 11, 2009 (6 pages, last page blank except for heading at top and web address at bottom).*
European Search Report for application No. 04253205, Oct. 19, 2004, 3 pages.
Li et al., "A novel injectable bioactive bone cement for spinal surgery: a developmental and preclinical study," XP-002301270, Mar. 2000, 164-170.
Neurosurg. Focus, vol. 10, Apr. 2001; Article entitled, "Bone graft substitutes for the promotion of spinal arthrodesis", p. 1-5 Gregory A. Helm et al.
Product Catalogue from DePuy AcroMed entitled, Surgical Titanium Mesh®, pp. 1-17.
European Search Report for European Application No. 03252016.5-1219-, Aug. 5, 2003, 5 pages.
Bunker, B.C., et al., "Ceramic Thin-Film Formation on Functionalized Interfaces through Biomimetic Processing"; Science, American Association For The Advancement Of Science, U.S. vol. 265, Apr. 1, 1994, pp. 48-55. 14.
Article from Society For Biomaterials ©2000, entitled, "Bone Ingrowth Into Phosphonylated PEEK Rabbit Tibial Implants". J M Allan et al.
Agrawal et al., "Protein release kinetics of a biodegradable implant for fracture non-unions," Biomaterials, 16 (16), 1255-1260 (1995). 1.
Radin et al., "Calcium phosphate ceramic coatings as carriers of vancomycin," Biomaterials, 18 (11), 777-782 (1997). Ducheyne et al., "The effect of calcium phosphase ceramic composition and structure on in vitro behavior. I. dissolution," Journal of Biomedical Materials Research, 27, 25-34 (1993).
Liu et al., "Biomimetic coprecipitation of calcium phosphate and bovine serum albumin on titanium alloy," Journal of Biomedical Materials Research, 56 (1), 327-335 (2001).
Wen et al., "Incorporation of bovine serum albumin in calcium phosphate coating on titanium," Journal of Biomedical Materials Research, 46 (2), 245-252 (1999). 2.
Meraw et al., "Use of alendronate in peri-implant defect regeneration," Journal of Periodontol, 70 (2), 151-158 (1999).
Liu et al., "Proteins incorporated into biomimetically prepared calcium phosphate coatings modulate their mechanical strength and dissolution rate," Biomaterials, 24, 65-70 (2003).
De Bruijn et al., "New developments in implant coatings: biomimetics and tissue engineering," Biomaterials in Surgery, Walenkamp, Stuttgart: Geory Thieme Verlag, 77-82 (1998).

* cited by examiner

Primary Examiner — Walter B Aughenbaugh
(74) Attorney, Agent, or Firm — Barnes & Thornburg LLP

(57) ABSTRACT

An implantable article including a biocompatible substrate and a bioactive strontium-substituted calcium phosphate ceramic apatite coating chemically bonded to at least a portion of the surface of the biocompatible substrate, wherein the strontium-substituted calcium phosphate ceramic apatite coating includes nanopores, nanocrystals and strontium ions, and includes a hexagonal crystal structure of apatite having a molar ratio of strontium ions to calcium ions of about 0.0001 to about 0.5, and the strontium ions inhibit bone resorption in vitro and enhance bone formation in vivo so that the implantable article exhibits enhance fixation and bone ingrowth in and around the implantable article.

19 Claims, No Drawings

STRONTIUM-SUBSTITUTED APATITE COATING

CROSS-REFERENCE TO RELATED APPLICATIONS

This patent application is a divisional of U.S. patent application Ser. No. 10/448,685, filed May 30, 2003 now U.S. Pat. No. 6,905,723.

FIELD OF THE INVENTION

This invention pertains to a method of preparing an implantable article.

BACKGROUND OF THE INVENTION

It is desirable to apply mineralized and/or ceramic coatings to a variety of articles. Biological implants (e.g., medical implants) represent one class of articles to which such coatings are frequently applied. The substrate to which such a coating is applied is usually a metal or a plastic, but the coating can be applied to other substrates such as ceramic and silicon.

Biological implants, such as joint and dental prostheses, usually must be permanently affixed or anchored within bone. In some instances it is acceptable to use a bone cement to affix the prosthesis within bone. In the case of many joint prostheses, however, it is now more common to affix the joint prosthesis by encouraging natural bone ingrowth in and around the prosthesis. Bone-to-implant interfaces that result from natural bone ingrowth tend to be stronger over time and more permanent than are bone cement-prosthesis bonds.

Optimal bone ingrowth requires that natural bone grow into and around the prosthesis to be implanted. Bone ingrowth and prosthesis fixation can be enhanced by providing irregular beaded or porous surfaces on the implant. Although various materials, including titanium alloys, are biocompatible, they are not necessarily bioactive because they can neither conduct bone formation nor form chemical bonds with bone.

Thus, enhanced fixation of implants within bone can be attained by coating the implant with a bioactive mineralized and/or ceramic material. Such coatings have been shown to encourage more rapid bone ingrowth in and around the prosthesis.

Various techniques are used to apply mineralized and/or ceramic coatings to bioimplantable substrates. These coatings are typically made of ceramics and tend to be characterized by a relatively large crystal size. These coatings can be applied by a variety of techniques including plasma spraying, ion implantation, and sol-gel processing. These coating methods, although relatively widely used, do have some drawbacks. For example, the applied coatings tend to possess micropores and macropores, and they can be relatively thick and brittle. These coatings can also possess chemical defects, and they do not always adhere well to substrates. Finally, such coatings are not evenly and uniformly applied to surfaces with complex geometries, such as porous surfaces with undercut regions. Moreover, surfaces having such complex geometries sometimes are not completely coated.

It has been well documented that calcium phosphate ceramics, especially hydroxyapatite, can conduct bone formation. Hydroxyapatite ceramic has been successfully applied as a coating on cementless metallic implants to achieve quick and strong fixation. Thermal plasma spraying is one of the more common methods used to produce hydroxyapatite coatings. However, the resulting plasma-sprayed hydroxyapatite coating is of relatively low density and is not uniform in structure or composition. The adhesion between the coating and substrate is generally not very strong, especially after long-term exposure within the body. The generation of hard ceramic particles, resulting from the degradation of thermal plasma sprayed coating, and coating delamination, are major concerns.

Low temperature processes have also been implemented to produce apatite ceramic coatings using water-based solutions. Since aqueous solutions can reach any open space, these low-temperature processes can be efficiently used in the case of substrates with complex surface geometries. The hydroxyapatite coating that is formed from this solution can be more biologically friendly to bone tissue than is the plasma-sprayed hydroxyapatite coating which is produced by a high temperature process. However, currently known low temperature processes typically require pretreatment of the substrate.

One example of an aqueous system-based coating technique is disclosed in U.S. Pat. No. 5,205,921 in which bioactive ceramic coatings are electrodeposited upon a substrate. Bunker et al., *Science,* 264: 48-55 (1994), disclose a technique for applying an octacalcium phosphate upon a substrate by immersing the substrate in a solution containing calcium chloride after surface treating the substrate with a material such as chlorosilane. Other techniques, such as disclosed in Japanese Patent Application No. 8-40711, form a hydroxyapatite coating by exposing the substrate to calcium phosphate in a pressure reactor. U.S. Pat. No. 5,188,670 discloses a technique for forming a hydroxyapatite coating on a substrate by directing a stream of liquid containing hydroxyapatite particles to apply a fibrous, crystalline coating of hydroxyapatite to the substrate.

The bioactivity and stability of synthetic apatite ceramics, such as the calcium phosphate hydroxyapatites described above, have been improved upon by adding elements such as silicon, magnesium, fluorine, and strontium ions to the apatite to substitute for calcium. For example, U.S. Pat. No. 6,312,468 discloses a silicon-substituted apatite that is more bioactive than calcium phosphate hydroxyapatite, and can be used as a synthetic bone material. Also, U.S. Pat. No. 6,338,810 discloses a biocompatible strontium-substituted apatite ceramic produced by mixing calcium phosphate and strontium phosphate powders that can be used, for example, in bone prosthetics. A bioactive bone cement comprising a strontium-containing hydroxyapatite is disclosed in International Patent Application No. WO 01/49327. U.S. Patent Application Publication No. 2002/0127711 A1 discloses a calcium hydroxyapatite matrix used as a support for implanting bone cells grown ex vivo, in which calcium can be replaced by other ions such as barium, strontium, and lead. U.S. Pat. No. 5,441,536 discloses a method for producing an implant involving coating the implant with calcium phosphate that is not apatite, and using hydrothermal treatment to convert the calcium phosphate into an apatite ceramic layer. The calcium ions in the calcium phosphate layer can be substituted with strontium, magnesium, chlorine, fluorine, or carbonate ions during the transformation of the non-apatitic calcium phosphate to apatite.

Despite the existence of numerous ceramic coatings and the various processes for producing such coatings, there remains a need for additional methods of making implantable articles that desirably have improved bioactive ceramic coatings. The invention provides such a method for making implantable articles. These and other advantages of the invention, as well as additional inventive features, will be apparent from the description of the invention provided herein.

BRIEF SUMMARY OF THE INVENTION

The invention provides a method of preparing an implantable article comprising (a) providing a biocompatible substrate with a surface that is not coated with a calcium-containing compound, (b) incubating at least a portion of a surface of the biocompatible substrate with a composition comprising (i) strontium ions in a concentration of about 0.1 mM to about 10 mM, (ii) calcium ions in a concentration of about 0.1 mM to about 10 mM, (iii) phosphate ions in a concentration of about 0.1 mM to about 10 mM, and (iv) a liquid carrier, wherein the pH of the composition is about 5 to about 8, and (c) removing the liquid carrier from the biocompatible substrate to yield an implantable article with a strontium-substituted ceramic apatite coating chemically bonded to at least a portion of the surface of the biocompatible substrate.

DETAILED DESCRIPTION OF THE INVENTION

The invention provides a method of preparing an implantable article. The method comprises (a) providing a biocompatible substrate with a surface that is not coated with a calcium-containing compound, (b) incubating at least a portion of a surface of the biocompatible substrate with a composition comprising (i) strontium ions, (ii) calcium ions, (iii) phosphate ions, and (iv) a liquid carrier, and (c) removing the liquid carrier from the biocompatible substrate to yield an implantable article with a strontium-substituted ceramic apatite coating chemically bonded to at least a portion of the surface of the biocompatible substrate.

The term "implantable article" as used herein refers to any object or device that can be inserted or embedded into or grafted onto an animal (especially human) body, or any part thereof, and that is designed for biomedical use. The implantable article, for example, can be a bone substitute, a joint prosthesis, a dental implant (prosthodontics), a maxillofacial implant, a vertebral surgery aid, a transcutaneous device (stoma or the like), or other medical or cosmetic device. Such implantable articles can serve as a bone replacement or bone reinforcement, as well as a means of fixing a device to a particular bone.

By "biocompatible substrate" is meant any object or device that is compatible with the animal (especially human) body into which the object or device is inserted or embedded or with the body onto which the object or device is grafted, such that the object or device will not cause an adverse immune response in the body. The biocompatible substrate can comprise, consist essentially of, or consist of any suitable material(s), such as silicon, metals, ceramics, or polymers. Biocompatible metals include titanium, tantalum, niobium, zirconium, and alloys thereof (e.g., titanium alloys and tantalum alloys), as well as cobalt, cobalt-chromium alloys, and stainless steel. Biocompatible polymers can be natural or synthetic polymers, such as polyethylene (e.g., ultrahigh molecular weight polyethylene or polyethylene oxide), polypropylene, polytetrafluoroethylene, polyglycolic acid, polylactic acid, other polysaccharides, and copolymers of any of the foregoing (e.g., copolymers of polylactic acid and polyglycol acid). Preferably, the biocompatible substrate comprises, consists essentially of, or consists of a biocompatible metal. More preferably, the biocompatible substrate comprises, consists essentially of, or consists of titanium and cobalt. The biocompatible substrate can be any suitable portion of the implantable article, preferably a component of a prosthesis (particularly a joint prosthesis). Suitable biocompatible substrates are described in U.S. Pat. Nos. 6,139,585 and 6,143,948.

The biocompatible substrate can be modified in a variety of ways prior to being coated with the bioactive surface or ceramic coating. For example, the biocompatible substrate can be modified with respect to surface roughness in order to facilitate the adherence of the bioactive strontium-substituted ceramic apatite coating to the biocompatible substrate. Methods of modifying the surface roughness of a biocompatible substrate are known in the art and include, for instance, acid etching and grit blasting. The biocompatible substrate typically is subjected to a cleaning process (e.g., after modifying the surface roughness), such as ultrasonic cleaning. Such cleaning processes are also known in the art. Preferably, the biocompatible substrate is grit-blasted and then ultrasonically cleaned. While the biocompatible substrate may be modified in any suitable manner to facilitate adherence of the ceramic coating to the substrate, the biocompatible substrate is not coated with a calcium-containing compound prior to being coated with the bioactive strontium-substituted ceramic apatite coating.

At least a portion of the surface of the biocompatible substrate (e.g., the entire surface of the biocompatible substrate) is coated with a bioactive strontium-substituted ceramic apatite coating. By "bioactive" is meant having the ability to effect local tissue activity, for instance, by improving local bone formation or by preventing the onset and proliferation of microbial species. The bioactive surface coating is a ceramic apatite coating, i.e., a coating that is predominantly of ceramic material(s). The bioactive ceramic apatite coating can comprise, consist essentially of, or consist of any suitable ceramic material(s). Suitable ceramic materials include calcium phosphate, strontium chloride, alumina, bioglass, and composite materials containing one or more of a biodegradable alkali metal salt, alkaline earth metal salt, or transition metal salt. The ceramic material contains apatite (e.g., calcium phosphate hydroxyapatite, carbonated apatite, carbonated hydroxyapatite), in which strontium ions are substituted for at least some of the calcium ions (i.e., a "strontium-substituted" apatite). The term "apatite" as used herein refers to any of a group of calcium phosphate minerals occurring variously as hexagonal crystals, as granular masses, or in fine-grained masses. Bioactive ceramic apatite coatings are generally described in U.S. Pat. Nos. 6,139,585 and 6,143,948. The bioactive strontium-substituted ceramic apatite coating described herein is desirable in that strontium ions inhibit bone resorption in vitro and enhance bone formation in vivo.

The bioactive strontium-substituted ceramic apatite coating can comprise multiple (i.e., two or more) layers, which may be the same or different. The bioactive strontium-substituted ceramic apatite coating can be of any suitable thickness. The bioactive strontium-substituted ceramic apatite coating desirably has a thickness of about 0.005 μm or more (e.g., about 0.01 μm or more, about 0.1 μm or more, or about 0.2 μm or more). The bioactive strontium-substituted ceramic apatite coating also desirably has a thickness of about 50 μm or less (e.g., about 30 μm or less, about 20 μm or less, about 10 μm or less, or about 5 μm or less).

Preferably, the bioactive strontium-substituted ceramic apatite coating is a nanoporous ceramic coating. The term "nanoporous" as used herein refers to the coating having pores that are less than 1 μm in diameter. Also preferred is that the bioactive strontium-substituted ceramic apatite coating is nanocrystalline. The term "nanocrystalline" as used herein means having a crystal size of less than 1 μm.

The bioactive strontium-substituted ceramic apatite coating is chemically bonded to at least a portion of the surface of the biocompatible substrate. In accordance with the invention, the implantable article comprising a biocompatible substrate with a strontium-substituted ceramic apatite coating chemically bonded thereto is produced by incubating at least a portion of a surface of the biocompatible substrate with a composition comprising strontium, calcium, and phosphate ions and a liquid carrier, and removing the liquid carrier from the biocompatible substrate. The terms "strontium ions," "calcium ions," and "phosphate ions" refer to ions that include strontium, calcium, and phosphate group ions, respectively. The ions can be, for example, monovalent, divalent, or trivalent with respect to charge. The strontium and calcium ions preferably are divalent, i.e., $Sr^{2+}$ and $Ca^{2+}$. The phosphate ions preferably are $PO_4^{3-}$, $HPO_4^{2-}$, or $H_2PO_4^{-}$.

The concentrations of the strontium ions, the calcium ions, and the phosphate ions are independent, i.e., the concentrations can be the same or different, in the composition used to prepare the implantable article. The concentration of each of the strontium ions, calcium ions, and the phosphate ions in the composition independently is about 0.1 mM to about 10 mM. Preferably, the concentration of each is about 5 mM or less. More preferred is that the concentration of each is about 1.5 mM or less. Also preferred is that the concentration of each of the strontium ions, calcium ions, and phosphate ions is about 0.5 mM or more. Most preferably, the concentration of the strontium ions in the composition is about 0.5 mM to about 5 mM (e.g., about 0.5 mM, about 1.0 mM, or about 1.5 mM). The strontium-substituted ceramic apatite coating produced by incubating a biocompatible substrate with the composition described herein desirably contains a molar ratio of strontium ions to calcium ions of about 0.0001 (i.e., 1:10,000) to about 0.5 (i.e., about 1:2) (e.g., about 1:5,000 to about 1:2, about 1:2500 to about 1:5, about 1:1000 to about 1:5, about 1:500 to about 1:4, about 1:200 to about 1:4, about 1:50 to about 1:10, or about 1:30 to about 1:10).

The composition can further comprise additional components, substances, and chemical groups and ions. For example, the composition can further comprise one or more substances selected from the group consisting of sodium ions, magnesium ions, carbonate ions, hydroxyl ions, chloride ions, fluoride ions, potassium, silicate, $SO_4^{2-}$, tris(hydroxymethyl)aminomethane, and mixtures thereof. Accordingly, the strontium-substituted bioactive ceramic apatite coating produced by the inventive method can contain the same components, substances, and chemical groups and ions. The composition and strontium-substituted bioactive ceramic apatite coating can contain any suitable ratios of components, substances, and chemical groups and ions. The strontium-substituted bioactive ceramic coating preferably contains strontium, calcium, phosphate groups, and chloride groups.

The liquid carrier can be any suitable aqueous or non-aqueous liquid in which at least strontium ions, calcium ions, and phosphate ions can be suspended or dissolved for delivery of these components to the biocompatible substrate and/or bioactive ceramic coating. Suitable liquid carriers include water, tris-buffered saline, phosphate-buffered saline, and the like. The liquid carrier preferably is a physiologically compatible carrier, more preferably water (e.g., purified or sterilized water).

The pH of the composition used to form the strontium-substituted bioactive ceramic apatite coating is between about 5 and about 8. Preferably, the pH is between about 6.5 and about 8 (e.g., about 7.5).

The incubation time with the composition in accordance with the inventive method typically is about 30 minutes or more. Suitable incubation times include about 1 hour or more, about 5 hours or more, about 10 hours or more, about 24 hours or more, about 48 hours or more, about 72 hours or more, and about 100 hours or more. The incubation time preferably is about 2 hours or more (e.g., about 2 hours to about 20 days, or about 12 hours to about 10 days). More preferably, the incubation time is about 24 hours or more (e.g., about 24 hours to about 20 days, or about 48 hours to about 10 days). The incubation time most preferably is about 72 hours or more (e.g. about 72 hours to about 20 days, or about 5 days to about 10 days). In general, longer incubation times provide greater concentrations of strontium ions incorporated into the bioactive surface or ceramic coating.

The temperature at which the incubation with the composition takes place can be any suitable temperature. The incubation temperature typically is about 20° C. to about 100° C. Ideally, the incubation temperature does not exceed the temperature at which biocompatible substrate or the strontium-substituted bioactive ceramic apatite coating is inactivated. The temperature at which the biocompatible substrate and/or the strontium-substituted bioactive ceramic apatite coating is inactivated or denatured depends upon the specific nature thereof. More preferably, the incubation temperature preferably is between about 30° C. and about 50° C. Most preferably, the incubation temperature is between about 37° C. and about 45° C.

In the inventive method, the liquid carrier can be removed from the biocompatible substrate by any suitable method. Typically, the liquid carrier is removed by drying at a temperature below the temperature at which the biocompatible substrate or the strontium-substituted bioactive ceramic apatite coating is inactivated. As mentioned above, this temperature depends upon the nature of the biocompatible substrate and/or the strontium-substituted bioactive ceramic apatite coating. The drying method can be freeze-drying (so long as the temperature and act of freeze-drying does not adversely affect the biocompatible substrate and/or strontium-substituted bioactive ceramic apatite coating). Alternatively, the drying can occur at a higher temperature, e.g., a temperature of about 20° C. or more, yet below the temperature at which the biocompatible substrate and/or strontium-substituted bioactive ceramic apatite coating is inactivated or denatured. The drying temperature desirably is about 20° C. to about 50° C. (e.g., about 30° C., about 40° C., or about 50° C.).

The liquid carrier also can be removed by rinsing the biocompatible substrate and/or strontium-substituted bioactive ceramic apatite coating with an appropriate liquid, especially an aqueous solution, and then drying the ceramic coating as described above. A preferred rinsing liquid is water (e.g., purified or sterilized water).

It may not be necessary to remove all of the liquid carrier from the biocompatible substrate and/or strontium-substituted bioactive ceramic apatite coating in order to provide a functional implantable article. Preferably, however, all or at least substantially all of the liquid carrier is removed from the biocompatible substrate and/or strontium-substituted bioactive ceramic apatite coating.

The inventive method of preparing an implantable article can include other steps. For instance, the inventive method can further comprise, after the incubation step (i.e., after incubating at least a portion of the biocompatible substrate with the composition as described above), a further incubation step with a second composition comprising a liquid carrier and one or more of (i) strontium ions, (ii) calcium ions, and/or (iii) phosphate ions. In other words, the biocompatible substrate can be incubated with a variety of compositions. Such additional compositions can be the same or different, for example, with respect to the concentration or types of the strontium ions, phosphate ions, or calcium ions. In this regard, the inventive methods can further comprise additional incubating steps that differ from the incubation step described above with respect to the number of elements (or components) that comprise the incubation composition, the concentration of each of the elements (or components) of the incubation composition, the pH of the incubation composition, the time of incubation, and/or the temperature at which the incubation occurs.

The composition used to form the bioactive strontium-substituted ceramic apatite coating can further comprise a biological agent. The term "biological agent" refers to any naturally-occurring or synthetic agent that has a biological effect. Suitable biological agents include proteins, lipids, (lipo)polysaccharides, growth factors, cytostatic agents, hormones, antibiotics, anti-infective agents, anti-allergenic agents, anti-inflammatory agents, progestational agents, humoral agents, antipyretic agents, and nutritional agents. Preferably, the biological agent is an osteoinductive substance, osteoconductive substance, or a substance that is both osteoinductive and osteoconductive. The term "osteoinductive" as used herein refers to an agent that promotes mitogenesis of undifferentiated perivascular mesenchymal cells leading to the formation of osteoprogenitor cells with the capacity to form new bone. The term "osteoconductive" as used herein means promoting the facilitation of blood vessel incursion and new bone formation into a defined passive trellis structure. In other words, "osteoconductive" generally refers to factors that create a favorable environment for new bone growth and apposition, while "osteoinductive" generally refers to factors that stimulate, either directly or indirectly, the new bone growth. The term "apposition" as used herein refers to bone formation directly on the bioactive surface. The biological agent that is osteoinductive, osteoconductive, or both is preferably a protein.

Osteoinductive proteins are known in the art and include, for example, Bone Morphogenic Protein (BMP) and Osteogenic Protein-1 (OP-1; BMP-7). Osteoconductive proteins are also known in the art and include, for example, extracellular matrix proteins, such as collagen, antimicrobial and anti-inflammatory proteins, and blood-clotting factors. Proteins that are both osteoinductive and osteoconductive include, for instance, BMP and OP-1. Preferably, the protein is a non-collagenous bone protein, wherein the term "non-collagenous" means that the protein is not collagen. Non-collagenous bone proteins include, for example, osteonectin, osteopontin, osteocalcin, and bone sialoprotein. Also preferred is that the protein is a growth factor, such as Fibroblast Growth Factor (FGF), Transforming Growth Factor-$\beta$ (TGF-$\beta$), Platelet-Derived Growth Factor (PDGF), Insulin Growth Factor (IGF), and family members of any of the foregoing. Suitable biological agents also include antibiotics, such as vancomycin, penicillin, tetracycline, chlortetracycline, bacitracin, nystatin, streptomycin, neomycin, polymyxin, gramicidin, oxytetracycline, chloramphenicol, and erythromycin.

The biological agent preferably is incorporated into the bioactive strontium-substituted ceramic apatite coating. By "incorporated" it is meant that the biological agent is chemically and/or electrostatically bonded to, mechanically fixed to, and/or impregnated or entrapped within the bioactive surface or ceramic coating. The biological agent also can be bound or attached to the bioactive surface or the surface of the ceramic coating.

The biological agent can be present in any suitable concentration in the bioactive strontium-substituted ceramic apatite coating. Preferably, the concentration of the biological agent incorporated into the bioactive strontium-substituted ceramic apatite coating is about 0.001 ng or more biological agent per mg coating when the biological agent is a growth factor. More preferably, the concentration of the biological agent incorporated into the bioactive strontium-substituted ceramic apatite coating is about 0.01 ng or more per mg coating. Most preferably, the concentration of the biological agent incorporated into the bioactive strontium-substituted ceramic apatite coating is about 0.1 ng or more biological agent per mg coating (e.g., 1 ng or more biological agent per mg coating, or 10 ng or more biological agent per mg coating). Preferably, the concentration of the biological agent incorporated into the bioactive strontium-substituted ceramic apatite coating is about 1 µg per mg coating when the biological agent is an antibiotic or a protein that is not a growth factor. More preferably, the concentration of the biological agent incorporated into the bioactive strontium-substituted ceramic apatite coating is about 10 µg per mg coating when the biological agent is an antibiotic or a protein that is not a growth factor. Most preferably, the concentration of the biological agent incorporated into the bioactive strontium-substituted ceramic apatite coating is about 100 µg per mg coating when the biological agent is an antibiotic or a protein that is not a growth factor.

The total amount of the biological agent incorporated into the bioactive strontium-substituted ceramic apatite coating can be any suitable amount. Preferably, the total amount of the biological agent incorporated into the bioactive strontium-substituted ceramic apatite coating is at least 1 ng when the biological agent is a growth factor. More preferably, the total amount of the biological agent incorporated into the bioactive strontium-substituted ceramic apatite coating is at least 10 ng when the biological agent is a growth factor. Most preferably, the total amount of the biological agent incorporated into the bioactive strontium-substituted ceramic apatite coating is at least 100 ng when the biological agent is a growth factor. Preferably, the total amount of the biological agent incorporated into the bioactive strontium-substituted ceramic apatite coating is at least 1 µg when the biological agent is an antibiotic or a protein that is not a growth factor. More preferably, the total amount of the biological agent incorporated into the bioactive strontium-substituted ceramic apatite coating is at least 10 µg when the biological agent is an antibiotic or a protein that is not a growth factor. Most preferably, the total amount of the biological agent incorporated into the bioactive strontium-substituted ceramic apatite coating is at least 100 µg when the biological agent is an antibiotic or a protein that is not a growth factor.

Methods of determining the concentration of a biological agent incorporated into the bioactive strontium-substituted ceramic apatite coating are known in the art. Suitable methods include the bicinchnoinic protein assay (BCA), such as can be practiced with a BCA kit commercially available through Pierce Inc. (Rockford, Ill.).

The inventive method of preparing an implantable article yields an implantable article with a bioactive strontium-substituted ceramic apatite coating chemically bonded to a biocompatible substrate surface over at least a portion of the surface of the biocompatible substrate. The implantable article can be implanted in any suitable mammal, and the invention contemplates such a method of using the implantable article described herein. Suitable mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). The implantable article is especially preferred to be implanted in humans.

EXAMPLE

This example further illustrates the invention but, of course, should not be construed as in any way limiting its scope. This example demonstrates a method of making an implantable article with a bioactive strontium-substituted ceramic apatite coating on a biocompatible substrate.

Four aqueous compositions were prepared, one of which lacked strontium ions (Composition A), while the other three comprised 0.5 mM, 1.0 mM, and 1.5 mM strontium ions (Compositions B, C, and D), respectively. Each composition also contained about 130 mM to about 200 mM sodium ions, about 3.5 to about 7 mM potassium ions, about 0.05 mM to about 5 mM magnesium ions, about 0.1 mM to about 10 mM calcium ions, about 96 mM to about 250 mM chloride ions, about 0.1 mM to about 10 mM phosphate ($HPO_4^{2-}+H_2PO_4^-+PO_4^{3-}$) ions, about 0.05 mM to about 50 mM $HCO^{3-}$ ions, about 0 mM to about 1 mM $SO_4^{2-}$ ions, and water. The pH of the compositions at 37° C. was about 5 to about 8. Polished and grit-blasted titanium disks having a diameter of 25.4 mm and a thickness of 3 mm were incubated in each of these compositions at 45° C. The pH and temperature of each composition was monitored every 10 minutes, and the elemental component concentrations of each composition were measured. In this regard, atomic absorbance (AA) was used to quantify the amount of calcium and strontium ions in each composition, while UV-light spectrophotometry was used to measure the concentration of phosphate ions. The disks were incubated for different time periods from about 2 hours to about 7 days, at which time the disks were removed from contact with the compositions.

The coating formed on each of the titanium disks was analyzed by Thin-Film X-Ray Diffractometry (TF-XRD) and Scanning Electron Microscopy (SEM) linked with Energy-Dispersive Spectroscopy (EDS). For all compositions tested, TF-XRD demonstrated that the coating formed therefrom on the titanium disk consisted of pure apatite. All of the coatings demonstrated a similar XRD diffraction pattern, but a shift of diffraction peak at 2θ of around 26° was observed for the coatings produced from the compositions containing strontium ions (i.e., Compositions B-D), which increased with increasing strontium ion concentration. These results indicated that strontium was incorporated into the ceramic apatite coating and substituted for calcium ions in the ceramic apatite coating. SEM and EDS confirmed that incubation of the titanium disk in the composition containing 1.5 mM strontium ions produced a coating containing strontium.

The results of this example demonstrate that an implantable article comprising a biocompatible substrate and a bioactive strontium-substituted ceramic apatite coating chemically bonded to at least a portion of the surface of the biocompatible substrate can be prepared by incubating a biocompatible substrate with a surface that is not coated with a calcium-containing compound with a composition comprising (i) strontium ions in a concentration of about 0.1 mM to about 10 mM, (ii) calcium ions in a concentration of about 0.1 mM to about 10 mM, (iii) phosphate ions in a concentration of about 0.1 mM to about 10 mM, and (iv) a liquid carrier.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An implantable article comprising a biocompatible substrate having a bioactive ceramic calcium phosphate strontium apatite coating
    wherein the bioactive ceramic calcium phosphate strontium apatite includes nanopores, nanocrystals, and strontium ions, wherein the strontium ions inhibit bone resorption in vitro and enhance bone formation in vivo so that the implantable article exhibits enhanced fixation and bone ingrowth in and around the implantable article, and the bioactive ceramic calcium phosphate strontium apatite coating comprises a hexagonal crystal structure of apatite having a molar ratio of strontium to calcium of 0.0001 to about 0.5 so that a Thin-Film X-Ray Diffractometry (TF-XRD) diffraction pattern for the hexagonal crystal structure exhibits a 2θ diffraction peak shifted from a corresponding peak of pure apatite.

2. The implantable article of claim 1, wherein the biocompatible substrate comprises a material selected from the group consisting of silicon, metals, ceramics, and polymers.

3. The implantable article of claim 2, wherein the biocompatible substrate comprises a metal selected from the group consisting of titanium, titanium alloys, cobalt, cobalt-chromium alloys, tantalum, tantalum alloys, and stainless steel.

4. The implantable article of claim 2, wherein the biocompatible substrate comprises a polymer selected from the group consisting of ultrahigh molecular weight polyethylene, polyethylene oxide, polylactic acid, polyglycol acid, and copolymers of polylactic acid and polyglycol acid.

5. The implantable article of claim 1, wherein the biocompatible substrate is a component of a joint prosthesis.

6. The implantable article of claim 1, wherein the 2θ diffraction peak is shifted from the corresponding peak of pure apatite by about 26°.

7. The implantable article of claim 6, wherein the hexagonal crystal structure of apatite is derived from a method comprising removing a liquid carrier from a composition after incubating the biocompatible substrate for a period of time between about 2 hours and 7 days, the composition comprising:
   (i) strontium ions in a concentration of about 0.1 mM to about 10 mM,
   (ii) calcium ions in a concentration of about 0.1 mM to about 10 mM,
   (iii) phosphate ions in a concentration of about 0.1 mM to about 10 mM,
   (iv) a liquid carrier,
   (v) a biological agent, and
   (vi) having a pH of about 5 to about 8.

8. The implantable article of claim 1, wherein the bioactive ceramic calcium phosphate strontium apatite coating has a thickness of about 0.005 μm to about 50 μm.

9. The implantable article of claim 1, further comprising a biological agent selected from a group consisting of an osteoinductive substance, an osteoconductive substance, and a substance that is both osteoinductive and osteoconductive; wherein the biological agent is incorporated within the bioactive ceramic calcium phosphate strontium apatite coating without being denatured or inactivated.

10. The implantable article of claim 1, further comprising is an antibiotic incorporated within the bioactive ceramic calcium phosphate strontium apatite coating.

11. The implantable article of claim 9, wherein the concentration of the biological agent in the bioactive ceramic calcium phosphate strontium apatite coating coating is about 0.001 ng biological agent/mg coating or more.

12. The implantable article of claim 1, further comprising a substrate is selected from the group consisting of sodium ions, magnesium ions, hydroxyl ions, chloride ions, fluoride ions, and mixtures thereof.

13. An implantable article comprising a biocompatible substrate and a bioactive strontium-substituted calcium phosphate ceramic apatite coating chemically bonded to at least a portion of the surface of the biocompatible substrate, wherein the strontium-substituted ceramic calcium phosphate apatite coating includes nanopores, nanocrystals and strontium ions, and comprises a hexagonal crystal structure of apatite having a molar ratio of strontium ions to calcium ions of about 0.0001 to about 0.5 so that a Thin-Film X-Ray Diffractometry (TF-XRD) diffraction pattern for the hexagonal crystal structure exhibits a 2θ diffraction peak shifted from a corresponding peak of pure apatite, and the strontium ions inhibit bone resorption in vitro and enhance bone formation in vivo so that the implantable article exhibits enhanced fixation and bone ingrowth in and around the implantable article.

14. The implantable article of claim 13, wherein the biocompatible substrate comprises a material selected from the group consisting of silicon, metals, ceramics, and polymers.

15. The implantable article of claim 14, wherein the biocompatible substrate comprises a metal selected from the group consisting of titanium, titanium alloys, cobalt, cobalt-chromium alloys, tantalum, tantalum alloys, and stainless steel.

16. The implantable article of claim 14, wherein the biocompatible substrate comprises a polymer selected from the group consisting of ultrahigh molecular weight polyethylene, polyethylene oxide, polylactic acid, polyglycol acid, and copolymers of polylactic acid and polyglycol acid.

17. The implantable article of claim 13, wherein the biocompatible substrate is a component of a joint prosthesis.

18. The implantable article of claim 13, wherein the strontium-substituted calcium phosphate ceramic apatite coating has a thickness of about 0.005 μm to about 50 μm.

19. The implantable article of claim 13, wherein the strontium-substituted calcium phosphate ceramic apatite coating further comprises a biological agent.

\* \* \* \* \*